(12) United States Patent  
Simmons, Jr.

(10) Patent No.: US 7,879,098 B1
(45) Date of Patent: Feb. 1, 2011

(54) EXPANDABLE LORDOSIS STABILIZING CAGE

(76) Inventor: James W. Simmons, Jr., 16505 La Cantera Pkwy. #1121, San Antonio, TX (US) 78256

(*) Notice: Subject to any disclaimer, the term of this patent is extended or adjusted under 35 U.S.C. 154(b) by 0 days.

(21) Appl. No.: 11/471,882

(22) Filed: Jun. 21, 2006

Related U.S. Application Data

(60) Provisional application No. 60/728,228, filed on Oct. 19, 2005.

(51) Int. Cl.
*A61F 2/44* (2006.01)

(52) U.S. Cl. .................................................... 623/17.11

(58) Field of Classification Search .............. 623/17.11, 623/16.11, 17.16; 606/72, 73, 246–249
See application file for complete search history.

(56) References Cited

U.S. PATENT DOCUMENTS

| | | | | |
|---|---|---|---|---|
| 5,653,763 | A * | 8/1997 | Errico et al. | 623/17.11 |
| 6,117,174 | A | 9/2000 | Nolan | 623/17.11 |
| 6,129,763 | A * | 10/2000 | Chauvin et al. | 623/17.11 |
| 6,443,989 | B1 * | 9/2002 | Jackson | 623/17.15 |
| 6,454,807 | B1 * | 9/2002 | Jackson | 623/17.15 |
| 6,773,460 | B2 | 8/2004 | Jackson | 623/17.15 |
| 6,835,206 | B2 | 12/2004 | Jackson | 623/17.11 |
| 6,893,464 | B2 | 5/2005 | Kiester | 623/17.11 |
| 6,899,716 | B2 | 5/2005 | Cragg | 606/86 |
| 6,905,512 | B2 | 6/2005 | Paes et al. | 623/17.11 |
| 6,955,691 | B2 | 10/2005 | Chae et al. | 623/17.16 |
| 7,217,293 | B2 * | 5/2007 | Branch, Jr. | 623/17.16 |

* cited by examiner

*Primary Examiner*—Eduardo C Robert
*Assistant Examiner*—Tara R Carter
(74) *Attorney, Agent, or Firm*—Wayne J. Colton, Inc.

(57) ABSTRACT

An expandable stabilizing cage includes a body having a fixed cage section, an expandable cage section, formed as a number of elongate blocks, and a relief between the fixed and expandable cage sections. An orifice, which through the expandable cage section decreases in diameter with increased distance along the central axis of the body away from the fixed cage section, is provided through the body. The expandable stabilizing cage also includes a wafer, which, when inserted into the orifice through the body, causes outward flaring of the elongate bars for fixing the expandable stabilizing cage securely in place in the intervertebral disc space between two adjacent vertebral bodies. Upper elongate blocks have substantially planar upper surfaces. Lower elongate blocks have substantially planar lower surfaces. The surfaces may be provided with surface irregularities for facilitating stable engagement with adjacent vertebral bodies, exemplary irregularities including denticles, dimples, scores, grooves or small protuberances.

17 Claims, 18 Drawing Sheets

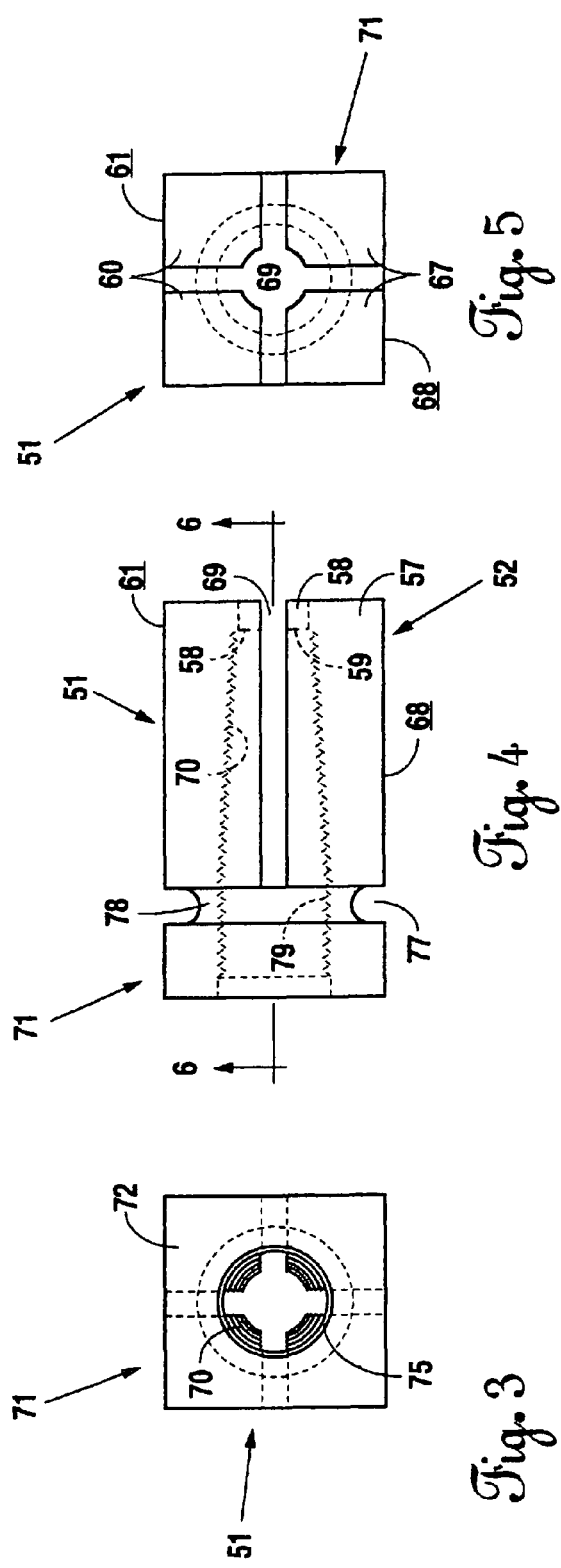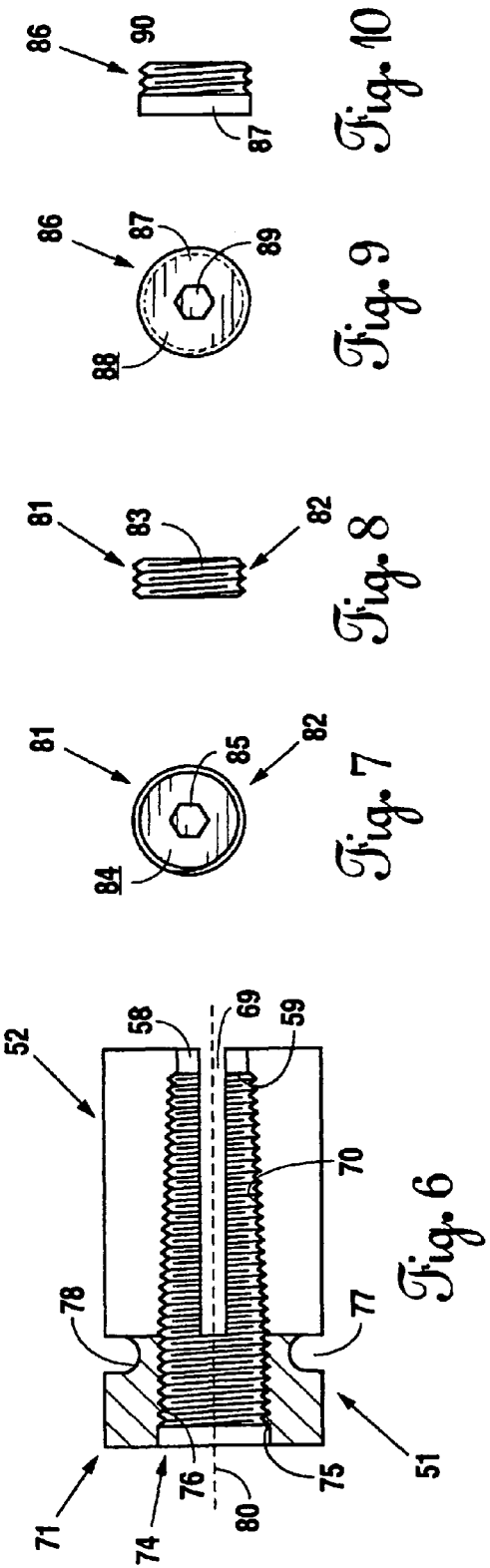

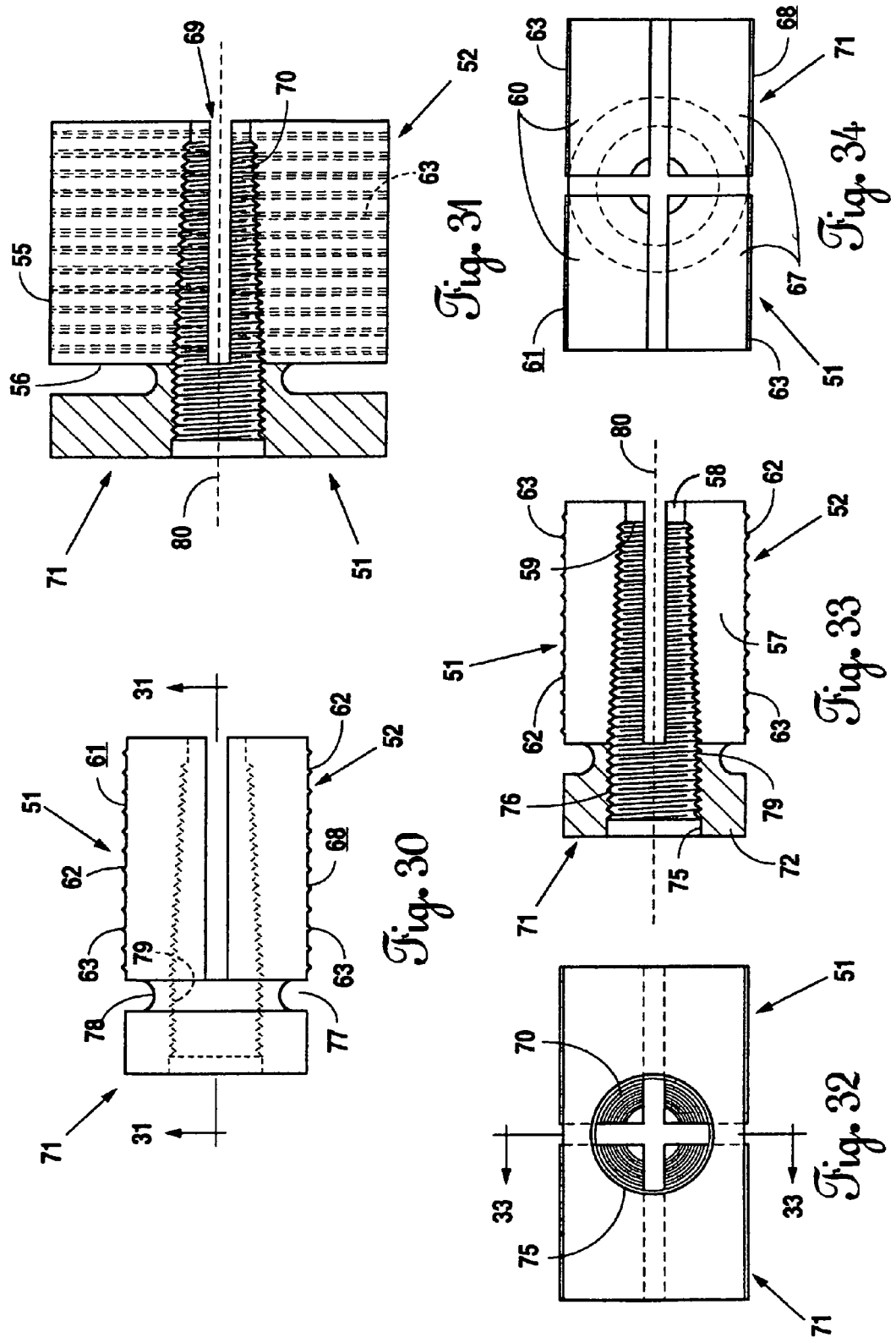

EXPANDABLE LORDOSIS STABILIZING CAGE

RELATED APPLICATION

This present application claims all available benefit, under 35 U.S.C. §119(e), to U.S. provisional patent application Ser. No. 60/728,228 filed Oct. 19, 2005. By this reference, the full disclosure, including the drawings, of U.S. provisional patent application Ser. No. 60/728,228 is incorporated herein as though now set forth in its entirety.

FIELD OF THE INVENTION

The present invention relates to medical devices. More particularly, the invention relates to an expandable stabilizing cage for replacement of a patient's intervertebral disc and fusion therethrough of the immediately superior and immediately inferior vertebral bodies, the expandable stabilizing cage being particularly adapted for either anterior or posterior insertion into the intervertebral space and for enhanced post-insertion stability.

BACKGROUND OF THE INVENTION

Patients suffering injury or deterioration of an intervertebral disc often require surgical intervention, which in some cases results in removal of the natural intervertebral disc and fusing of the adjacent superior and inferior vertebral bodies. In order to allow fusion with normal lordosis of the spine, however, it is necessary to mechanically stabilize the adjacent superior and inferior vertebral bodies in a desired relationship one to the other and, thereafter, to maintain the effected spatial relationship. As a consequence, medical technologists have developed a wide array of medical devices to this end. Unfortunately, the known devices are generally subject to inadvertent displacement during or following the fusion process due to ambulation of the patient and therefore generally require fairly invasive interventions to secure the devices in position in the intervertebral disc space. In particular, the known devices generally require the use of pedicle plates and pedicle screws or the like for maintenance of stable placement.

It is therefore an overriding object of the present invention to improve over the prior art by providing an expandable lordosis stabilizing cage that is inherently stable upon insertion into the intervertebral disc space of a patient under treatment. Additionally, it is an object of the present invention to provide such an expandable lordosis stabilizing cage that may be inserted into the patient's intervertebral disc space through either anterior or posterior surgical intervention.

SUMMARY OF THE INVENTION

In accordance with the foregoing objects, the present invention—an expandable stabilizing cage for insertion into the intervertebral disc space of a patient for establishing and maintaining a desired lordosis—generally comprises a body having a fixed cage section, an expandable cage section and a relief between the fixed cage section and the expandable cage section. The expandable cage section comprises a plurality of elongate blocks which are preferably connected to the fixed cage section by only a portion the end of each of the elongate blocks and which project longitudinally away from the fixed cage section. An orifice is provided through the body coaxial with a central longitudinal axis through the fixed cage section and the expandable cage section. The orifice through the expandable cage section decreases in diameter with increased distance along the central axis away from the fixed cage section. In at least one preferred embodiment of the present invention, the expandable stabilizing cage comprises a wafer, which, when inserted into the orifice through the body, causes outward flaring of the elongate bars for fixing the expandable stabilizing cage securely in place in the intervertebral disc space between two adjacent vertebral bodies.

Upper elongate blocks comprise a substantially planar upper surface and lower elongate blocks comprise a substantially planar lower surface. While still keeping with the critical requirement for substantially planar upper and lower surfaces, however, the surfaces may nonetheless be desirably provided surface irregularities for facilitating stable engagement of the elongate blocks with adjacent vertebral bodies. In particular (by way of example rather than limitation) the surface irregularities may comprise denticles, dimples, scores, grooves, small protuberances or the like.

Finally, many other features, objects and advantages of the present invention will be apparent to those of ordinary skill in the relevant arts, especially in light of the foregoing discussions and the following drawings, exemplary detailed description and appended claims.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein:

FIG. 3 shows, in a posterior end elevational view, the expandable lordosis stabilizing cage of FIG. 1;

FIG. 4 shows, in a right side elevational view, the expandable lordosis stabilizing cage of FIG. 1;

FIG. 5 shows, in an anterior end elevational view, the expandable lordosis stabilizing cage of FIG. 1;

FIG. 6 shows, in a cross sectional view taken through line 6-6 of FIG. 4, the expandable lordosis stabilizing cage of FIG. 1;

FIG. 7 shows, in an end view, the preferred embodiment of the expansion wafer utilized in implementation of the present invention;

FIG. 8 shows, in a side view, the preferred embodiment of the expansion wafer of FIG. 7;

FIG. 9 shows, in a posterior end view, the preferred embodiment of the end plug utilized in implementation of the present invention;

FIG. 10 shows, in a right side view, the end plug of FIG. 9;

FIG. 30 shows, in a right side elevational view, the expandable lordosis stabilizing cage of FIG. 28;

FIG. 31 shows, in a cross sectional view taken through line 31-31 of FIG. 30, the expandable lordosis stabilizing cage of FIG. 28;

FIG. 32 shows, in a posterior end elevational view, the expandable lordosis stabilizing cage of FIG. 28;

FIG. 33 shows, in a cross sectional view taken through line 33-33 of FIG. 32, the expandable lordosis stabilizing cage of FIG. 28;

FIG. 34 shows, in an anterior end elevational view, the expandable lordosis stabilizing cage of FIG. 28;

DETAILED DESCRIPTION OF THE PREFERRED EMBODIMENT

Although those of ordinary skill in the art will readily recognize many alternative embodiments, especially in light of the illustrations provided herein, this detailed description is exemplary of the preferred embodiment of the present invention, the scope of which is limited only by the claims appended hereto.

Figure 1:
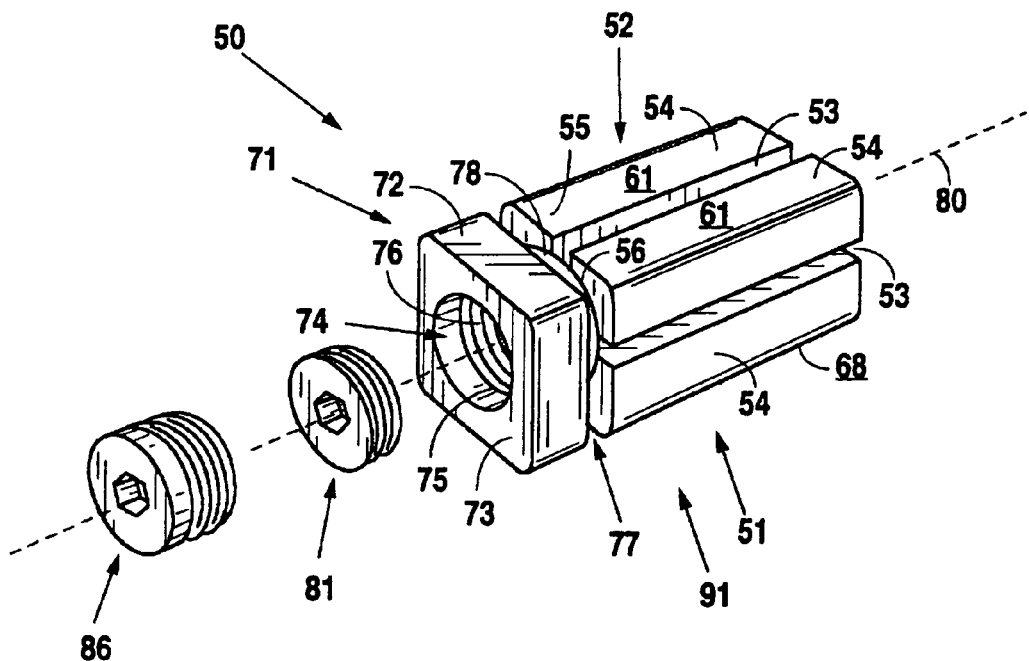
FIG. 1 shows, in a partially exploded perspective view, a first preferred embodiment of the expandable lordosis stabilizing cage of the present invention.
Figure 2:
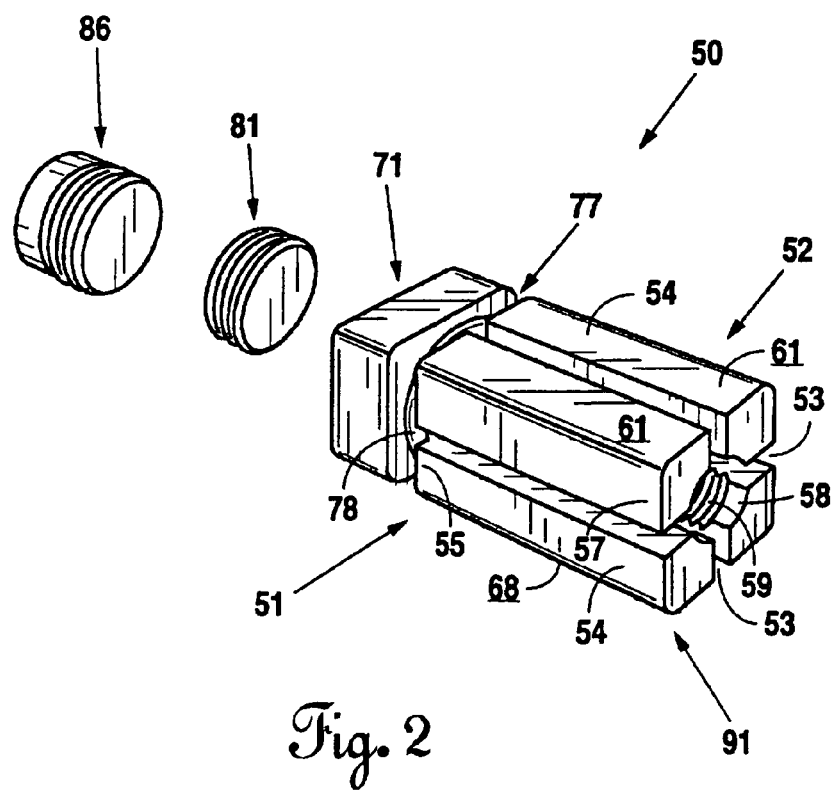
FIG. 2 shows, in a second partially exploded perspective view, the expandable lordosis stabilizing cage of FIG. 1.

Referring now to the figures, and to FIGS. 1 and 2 in particular, the lordosis stabilizing cage 50 of the present invention is shown to generally comprise a body 51 and an expansion wafer 81. As shown the figures, the body 51 comprises a generally rectilinear expandable cage section 52 and a fixed cage section 71 arranged adjacent one to the other along a central axis 80 running longitudinally through the body 51. As shown in FIGS. 1 through 6, the expandable cage section 52 comprises a plurality of elongate blocks 54 extending from their proximal ends 55 from the fixed cage section 71. As shown in the figures, the elongate blocks 54 are generally defined by the provision of slots 53 in the horizontal and vertical planes running through the central axis 80.

As shown in the figures, the elongate blocks 54 preferably comprise an upper pair 60 of elongate blocks 54 and lower pair 67 of elongate blocks 54. In order to promote stability of the lordosis stabilizing cage 50 after insertion into the intervertebral disc space 102 of a patient (as will be better understood further herein), it is critical to the present invention that each elongate block 54 of the upper pair 60 comprises a substantially planar upper surface 61. Likewise, it is critical to the present invention that each elongate block 54 of the lower pair 67 comprises a substantially planar lower surface 68. In this manner, expansion radially from the central axis 80 of the distal end 57 of each elongate block 54 (as will also be better understood further herein) results in engagement of a maximum surface area of the expandable cage section 52 of the lordosis stabilizing cage 50 with the adjacent superior vertebral body 95 and inferior vertebral body 100.

As shown in FIGS. 1 through 6, the fixed cage section 71 of the body 51 of the lordosis stabilizing cage 50 may comprise a nut 72, which although not critical to the present invention is preferably rectilinear in shape to facilitate manufacture of the lordosis stabilizing cage 50. In any case, the body 51 of the lordosis stabilizing cage 50 of the present invention comprises an orifice 74 arranged coaxially with the central axis 80 through the fixed cage 71. The orifice 74 through the fixed cage section 71 is cylindrical in shape and terminates into an orifice 69 through the expandable cage section 52. The orifice 69 through the expandable cage section 52, however, is shaped as a frustum of a cone, which frustum decreases in diameter with increased distance along the central axis 80 from the fixed cage section 71.

As a result of the described arrangement of orifice 74 and orifice 69 through the fixed cage section 71 and the expandable cage section 52, respectively, insertion of the expansion wafer 81 into and through the orifice 74 of the fixed cage section 71 and into and through the orifice 69 of the expandable cage section 52 results in the radially outward flaring of the distal ends 57 of the elongate blocks 54. In order to facilitate the desired flaring of the distal ends 57 of the elongate blocks 54, a relief 77 is provide in the body 51 of the lordosis stabilizing cage 50 in the area of intersection between the expandable cage section 52 and the fixed cage section 71. As shown in FIGS. 1 through 6, a suitable relief 77 may be implemented by providing an annulus 78 in the fixed cage section 71 at the location where the fixed cage section 71 interconnects with the expandable cage section 52. In this case, only a fractional, radially interior portion 56 of each of the proximal ends 55 of the elongate blocks 54 interconnect with the fixed cage section 71.

To facilitate generation of the radial force required for flaring of the distal ends 57 of the elongate blocks 54 during insertion of the expansion wafer 81, the orifice 69 through the expandable cage section 52 is preferably provided with interior threading 70. Likewise, the orifice 74 through the fixed cage section 71 is also provided with interior threading 76. As will be understood by those of ordinary skill in the art, the interior threading 76 of the orifice 74 through the fixed cage section 71 is tapped cylindrically through the orifice 74 to the portion interior 79 of the annulus 78. The interior threading 70 of the orifice 69 though the expandable cage section 52, however, is tapped as a frustum of a cone. In this implementation of the body 51 of the lordosis stabilizing cage 50, the expansion wafer 81 preferably comprises a set screw 82 or substantially equivalent structure having provided thereon circumferential threading 83 sized to mate with the interior threading 70,76 of the orifices 69, 74, respectively. Additionally, the set screw 82, or substantially equivalent structure, is provided at the central portion of one face 84 thereof with an Allen (hexagonal) socket 85 or any substantially equivalent drive such as, for example, a driver slot. In this manner, the surgeon may utilize the leverage of the threading 83 of the set screw 82 interplaying with the threading 70 of the orifice 69 through the expandable cage section 52 for generation of the outward radial force required to flare the distal ends 57 of the elongate blocks 54.

In order to prevent inadvertent driving of the expansion wafer 81 entirely through the orifice 69 of the expandable cage section 52, wafer stops 58 are preferably provided at the distal ends 57 of the elongate blocks 54. In one implementation of the present invention, shoulders 59 are provided at the termination of the interior threading 70 of the orifice 69 through the expandable cage section 52.

In at least one embodiment of the present invention, the lordosis stabilizing cage 50 comprises an end plug 86 for insertion into and closure of the orifice 74 of the fixed cage section 71 at the front face 73 of the fixed cage section 71. The end plug 86 is preferably implemented comprising a head 87 and a circumferentially threaded section 90. An Allen (hexagonal) socket 89 or any substantially equivalent drive such as, for example, a driver slot, is provided at or across the central portion of the face 88 of the head 87 of the end plug 86. The threading provided about the end plug 86 is, as will be appreciated by those of ordinary skill in the art, sized to mate with the interior threading 76 of the orifice 74 through the fixed cage section 71. In the preferred embodiment, however, the orifice 74 is provided with a shoulder 75 adjacent to the front face 73 of the fixed cage section 71 for flush acceptance into the orifice 74 of the head 87 of the end plug 86.

As shown in FIGS. 1 through 6, the first preferred embodiment of the lordosis stabilizing cage 50 of the present invention comprises a body 51 having a generally square cross section as pointed out in the figures by reference 91. Additionally, however, a second preferred embodiment comprises a generally rectangular cross section as denoted in the figures by reference 92 and particularly shown in FIGS. 28 through 34. The particular utility of each of these preferred embodiments will be detailed further herein.

Referring now to FIGS. 28, 29 and 37 through 39, it is noted that the present invention contemplates that the substantially planar upper surfaces 61 of the upper pair 60 of elongate blocks 54 and the substantially planar lower surfaces 68 of the lower pair 67 of elongate blocks 54 may be provided with surface irregularities 62. These surface irregularities 62 are provided to enhance secure engagement of the upper surfaces 61 and the lower surfaces 68 with the immediately superior vertebral body 95 and immediately inferior vertebral body 100 and should be limited to structures that enhance or facilitate maintenance of the position in the patient's intervertebral disc space 102 of the lordosis stabilizing cage 50. As shown in the figures, surface irregularities 62 meeting these requirements may comprise denticles 63, dimples 64, grooves or scores 65, bumps, nodules or other protuberances 66 or any substantially equivalent structure. In the case of irregularities 62 such as the denticles 63, it is noted that such structures are preferably transversely oriented such that maximum benefit of the irregularity 62 is directed towards maintenance of the anterior-posterior position of the inserted lordosis stabilizing cage 50 and also such that the irregularities 62 do not prevent or unduly hinder transverse spreading of the upper pair 60 or lower pair 67 of elongate blocks 54 during the expansion or flaring of the expandable cage section 52.

Figure 11:
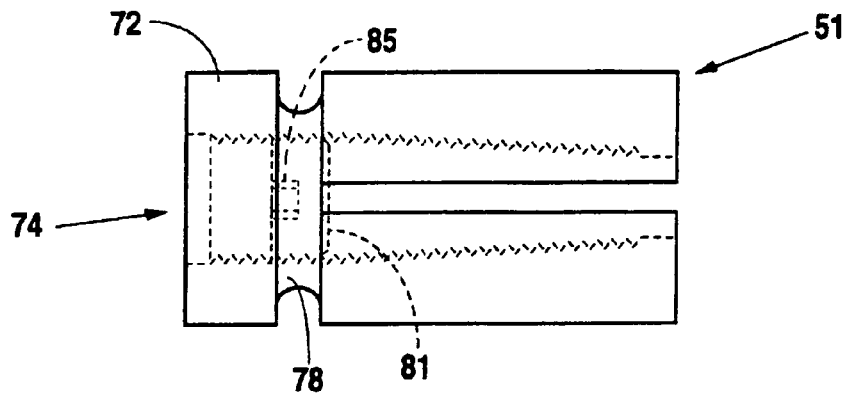
FIG. 11 shows, in a right side elevational view, the body of the expandable lordosis stabilizing cage of FIG. 1 with the wafer of FIGS. 7 and 8 inserted in preparation for a posterior insertion of the expandable lordosis stabilizing cage into the intervertebral disc space of a patient.

Referring now to FIGS. 11 through 18, the procedure for posterior insertion of the lordosis stabilizing cage 50 of the present invention into the decompressed intervertebral disc space 102 between a superior vertebra 94 and an inferior vertebra 99 of a section of assembled vertebrae 93 is described. As shown in FIG. 11, the body 51 of the lordosis stabilizing cage 50 is first prepared for posterior insertion by inserting the expansion wafer 81 (with the socket 85 of the expansion wafer 81 facing outward) into the orifice 74 of the nut 72 forming the fixed cage section 71. The expansion wafer 81 is threaded into the orifice 74 and positioned adjacent to the proximal end of the orifice 69 of the expandable cage section 52.

Figure 12:
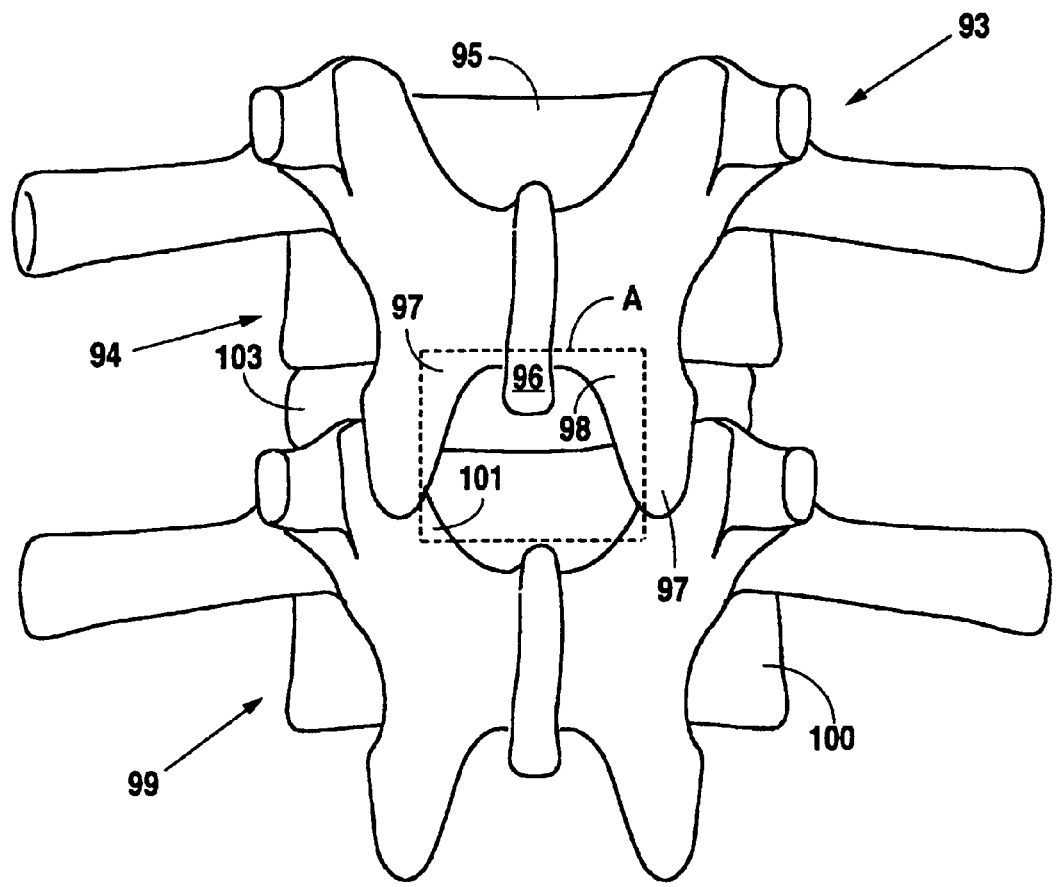
FIG. 12 shows, in a posterior elevational view, a section of assembled vertebrae, the view of FIG. 12 particularly detailing an area "A" from which vertebral structures are surgically excised prior to posterior insertion of the expandable lordosis stabilizing cage of the present invention.

With the body 51 of the lordosis stabilizing cage 50 prepared for insertion, the patient is prepared by surgically excising portions of the spinous process 96, the inferior articular process 97 and the lamina 98 of the superior vertebra 94 and portions of the lamina 101 of the inferior vertebra 99 falling generally within the area depicted with reference A in FIG. 12. Additionally, the superior vertebra 94 and inferior vertebra 99 are decompressed by surgical removal of the affected intervertebral disc 103.

Figure 13:
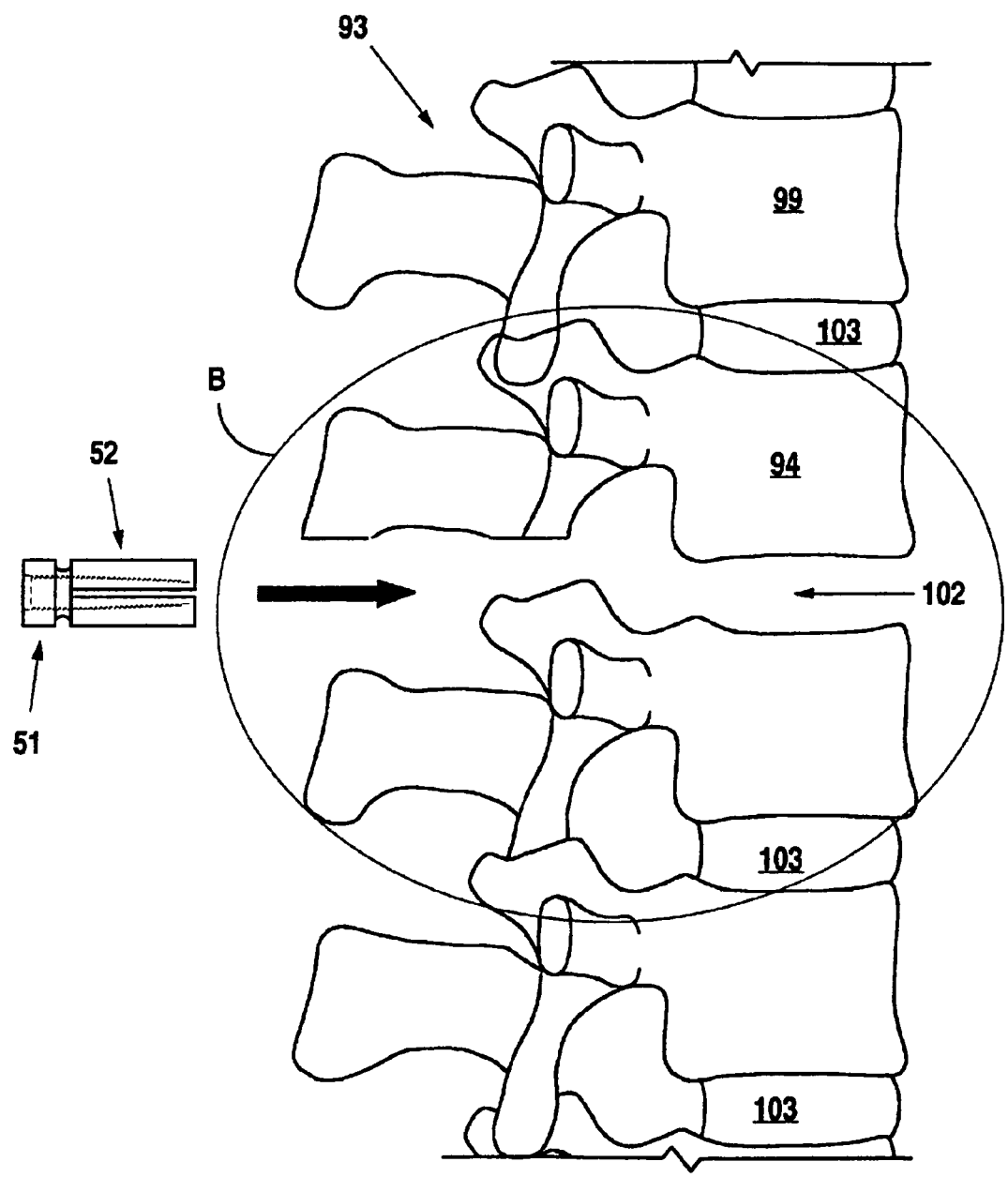
FIG. 13 shows, in a right side elevational view, the path of a posterior insertion of the expandable lordosis stabilizing cage of FIG. 1 into the decompressed intervertebral disc space of a patient.
Figure 14:
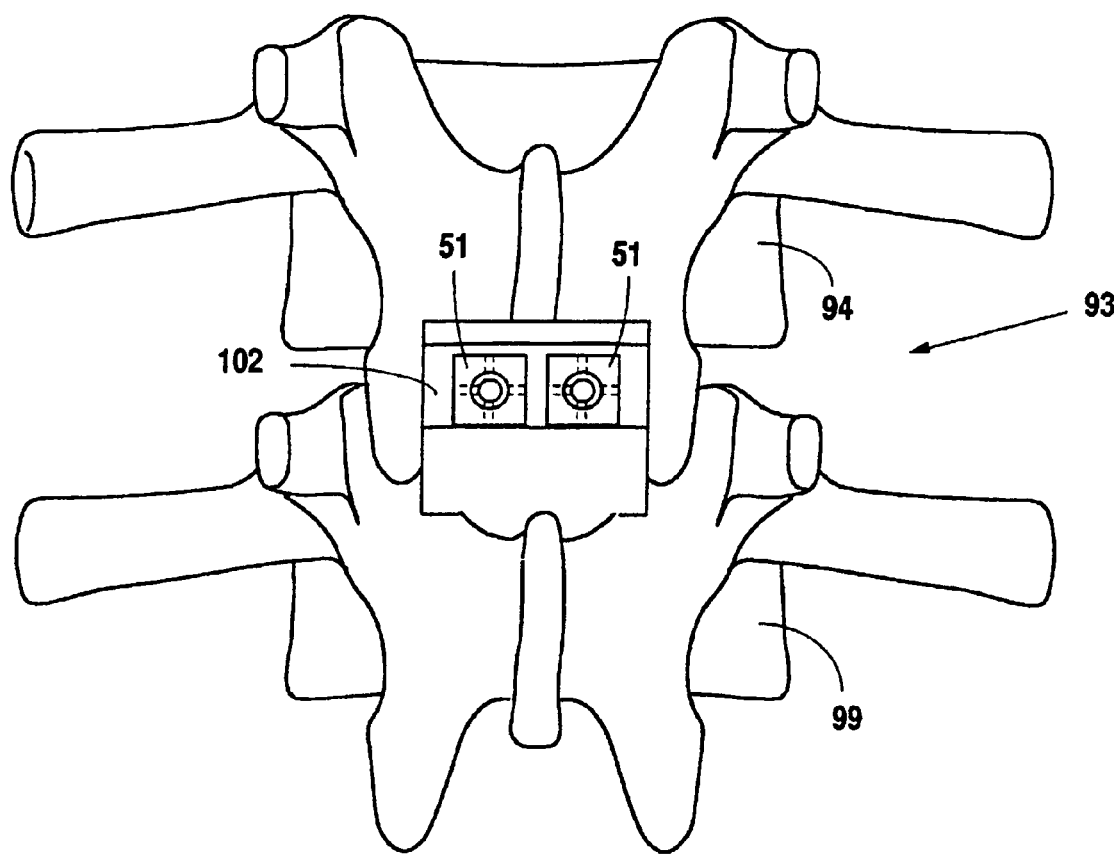
FIG. 14 shows, in a posterior elevational view of a section of assembled vertebrae, posterior placement of a pair of expandable lordosis stabilizing cages of FIG. 1 into the decompressed intervertebral disc space of a patient.
Figure 15:
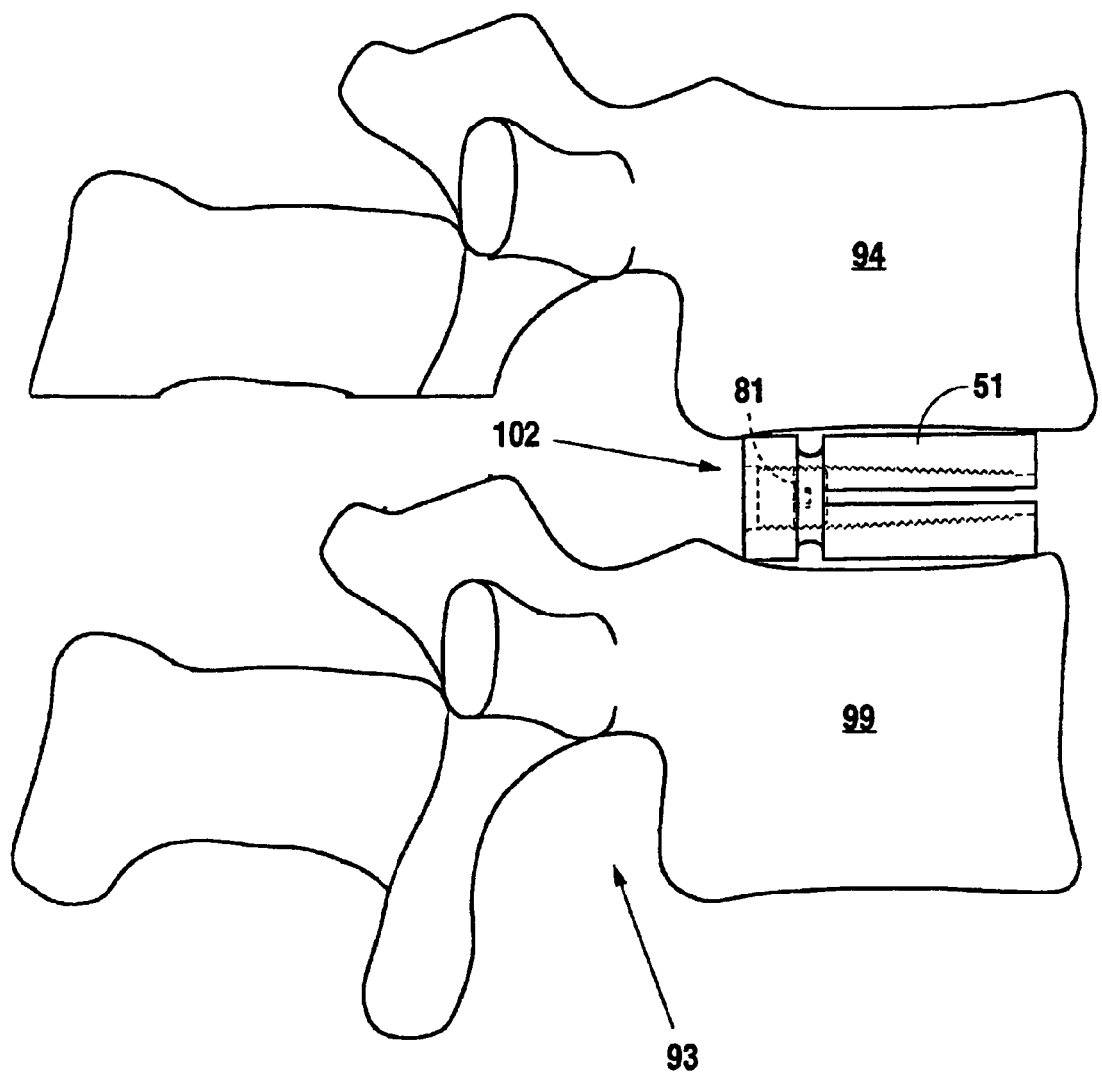
FIG. 15 shows, in a right side elevational detail view taken in detail area B of FIG. 13, placement into the decompressed intervertebral disc space of a patient of the body of the expandable lordosis stabilizing cage of FIG. 1 as prepared for posterior insertion according to FIG. 11.
Figure 16:
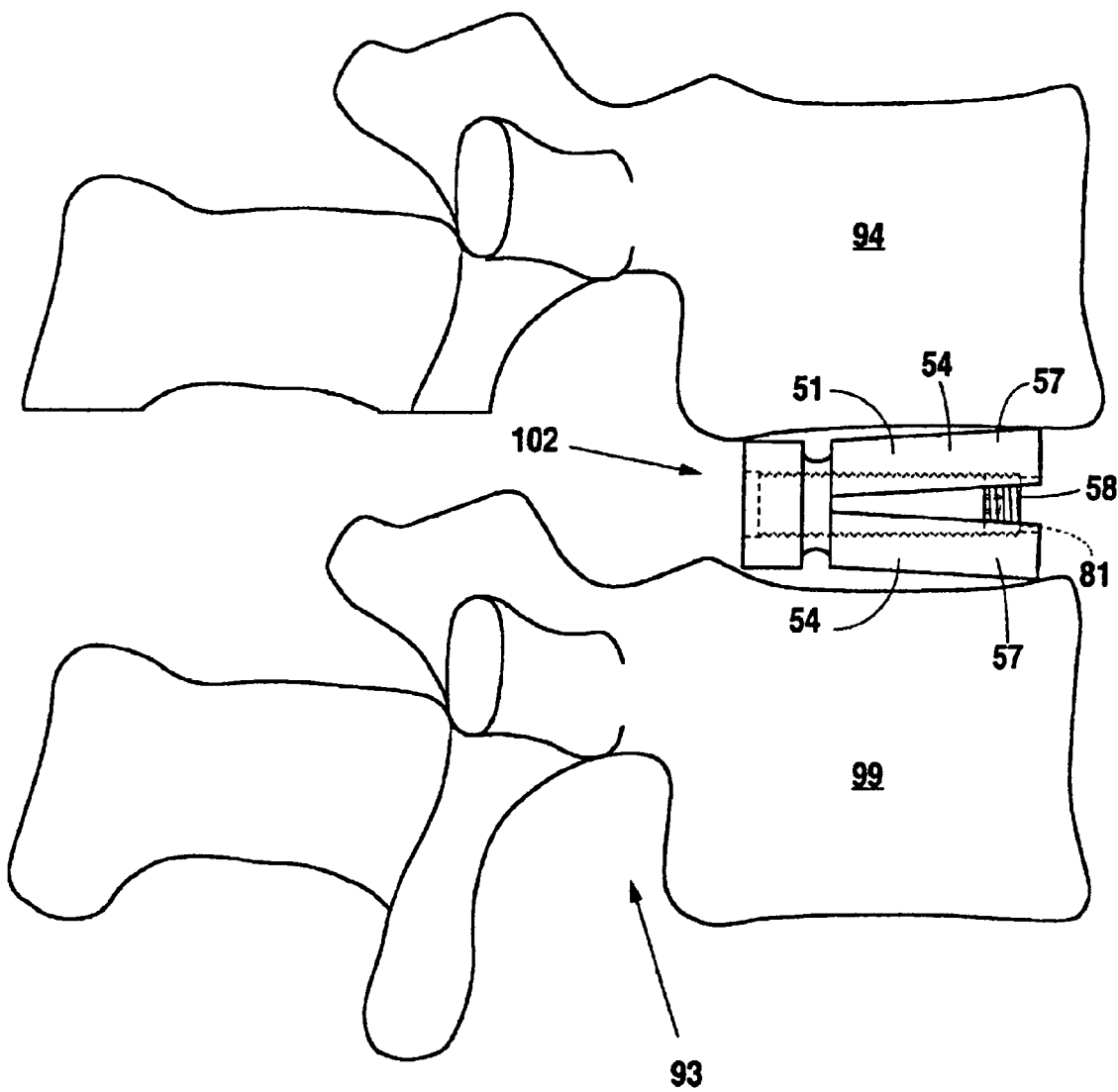
FIG. 16 shows, in a right side elevational detail view taken in detail area B of FIG. 13, expansion through operation of the expansion wafer of FIGS. 7 and 8 of the expandable cage section of the body of the expandable lordosis stabilizing cage of FIG. 1 after posterior insertion.

As shown in FIGS. 13 and 14, the prepared body 51 is then inserted (expandable cage section 52 first) into the decompressed intervertebral disc space 102. As particularly shown in FIG. 14, the posterior insertion of the lordosis stabilizing cage 50 will generally require the insertion of a pair of the generally square cross section stabilizing cages 91 in side-by-side position in order to avoid dangerous interaction with the spinal cord (not shown). In any case, with the previously prepared bodies 51 inserted into the intervertebral disc space 102 as depicted in FIG. 15, the surgeon then operates the expansion wafer 81 to translate the expansion wafer 81 through the orifice 69 of the expandable cage section 52 into position at the distal ends 57 of the elongate blocks 54, thereby causing radially outward flaring of the distal ends 57. The outward flaring of the distal ends 57 of the elongate blocks 54 in turn results in the wedging of the substantially planar surfaces 61 of the upper pair 60 of elongate blocks 54 and the substantially planar lower surfaces 68 of the lower pair 67 of elongate blocks 54 firmly between the superior vertebra 94 and inferior vertebra 99 bounding the intervertebral disc space 102.

Figure 17:
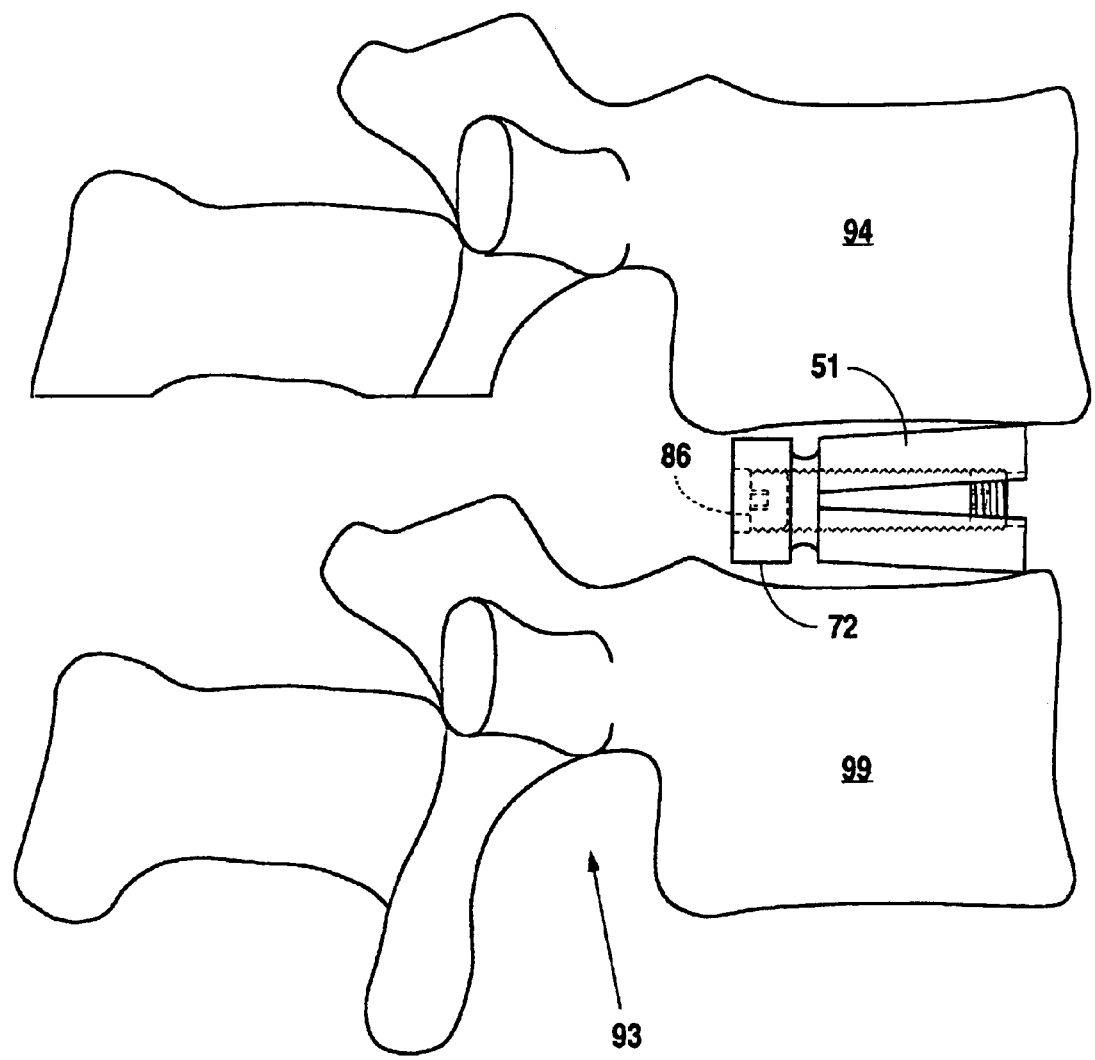
FIG. 17 shows, in a right side elevational detail view taken in detail area B of FIG. 13, final posterior insertion of the expandable lordosis stabilizing cage of FIG. 1.
Figure 18:
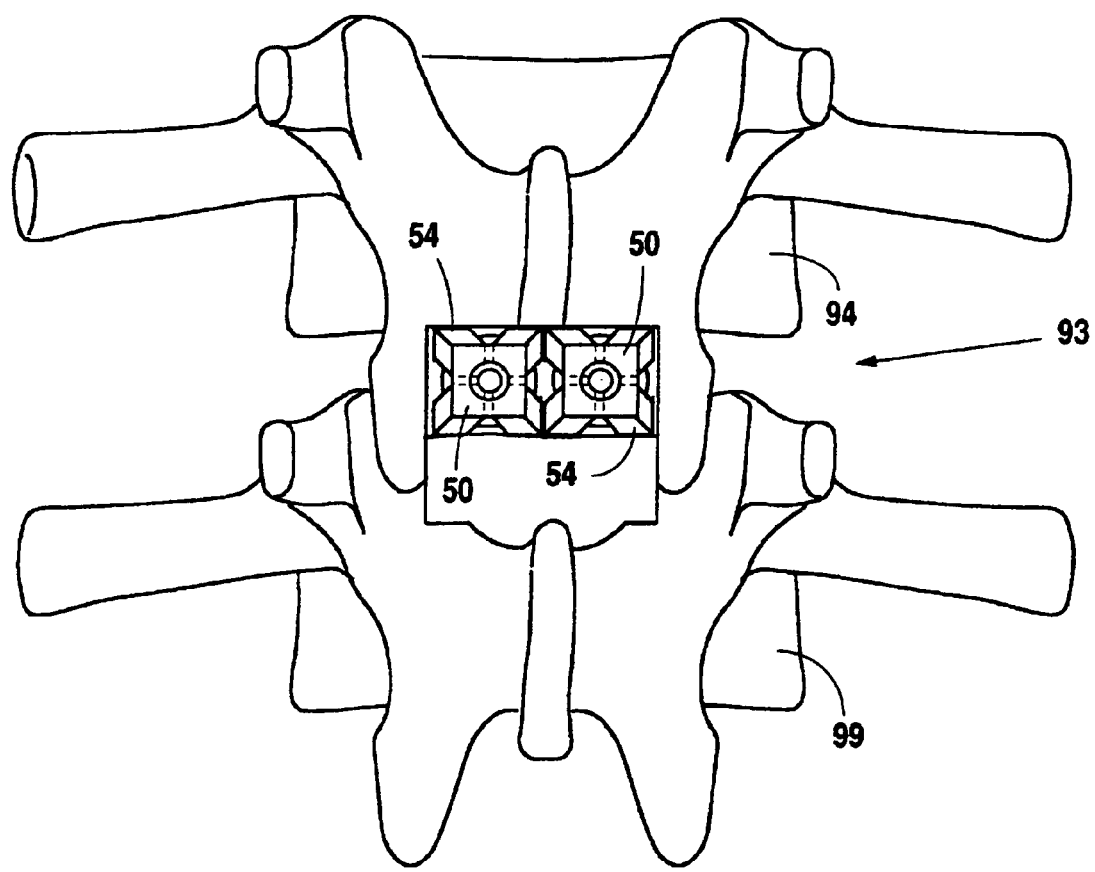
FIG. 18 shows, in a posterior elevational view of a section of assembled vertebrae, final posterior insertion of a pair of expandable lordosis stabilizing cages of FIG. 1.

As shown in FIG. 17, the surgeon then may insert the end plug 86 in place in the front face 73 of the fixed cage section 71. (Although not discussed in detail, it should be noted and understood by those of ordinary skill in the art that the surgeon will of course perform other steps during the conduct of the described procedures including, for example, packing of the lordosis stabilizing cage 50 and other areas in or about the intervertebral disc space 102 with bone, bone growth factors or the like.) Finally, as shown in FIG. 18, upon final placement of the lordosis stabilizing cages 50 of the present invention, the superior vertebra 94 and the inferior vertebra 99 will obtain and securely and stably maintain normal lordosis.

Figure 19:
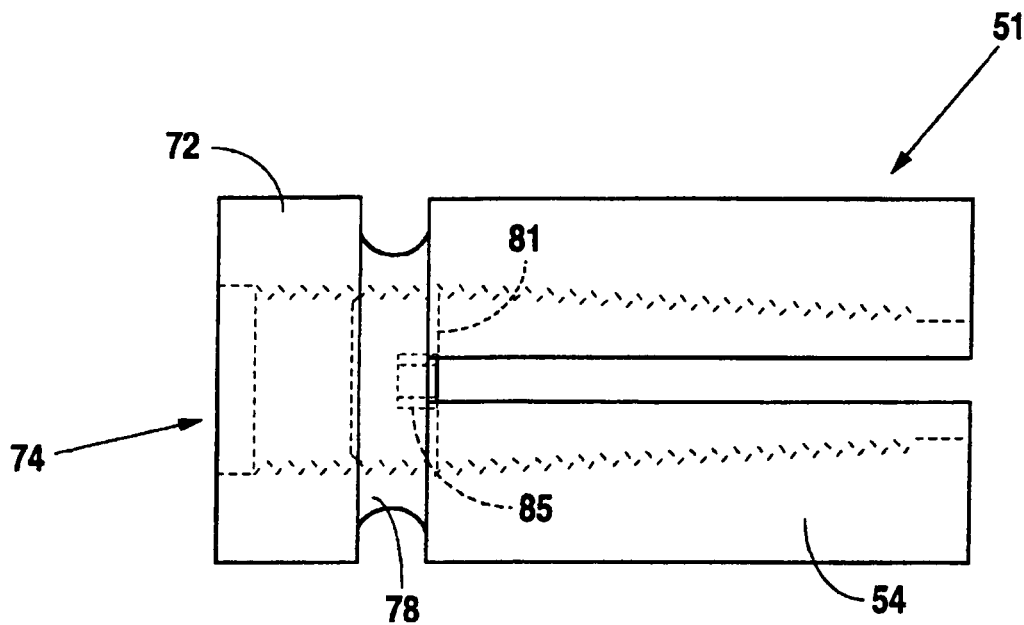
FIG. 19 shows, in a right side view, the body of the expandable lordosis stabilizing cage of FIG. 1 with the wafer of FIGS. 7 and 8 inserted in preparation for an anterior insertion of the expandable lordosis stabilizing cage into the intervertebral disc space of a patient.
Figure 20:
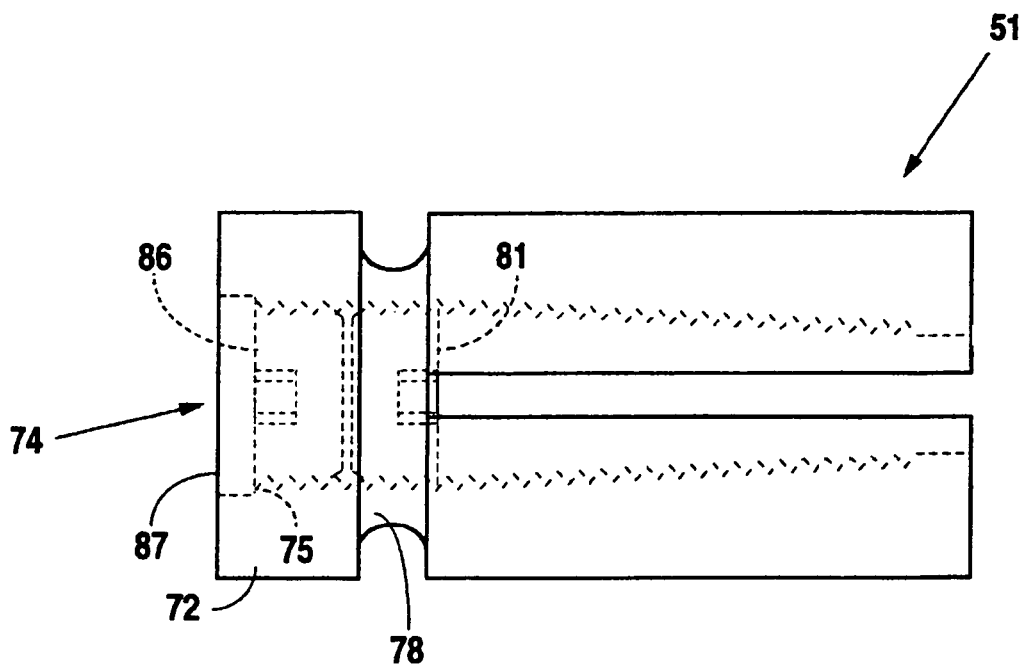
FIG. 20 shows, in a right side view, the body of the expandable lordosis stabilizing cage of FIG. 19 with the end plug of FIGS. 9 and 10 inserted in further preparation for an anterior insertion of the expandable lordosis stabilizing cage into the intervertebral disc space of a patient.
Figure 21:
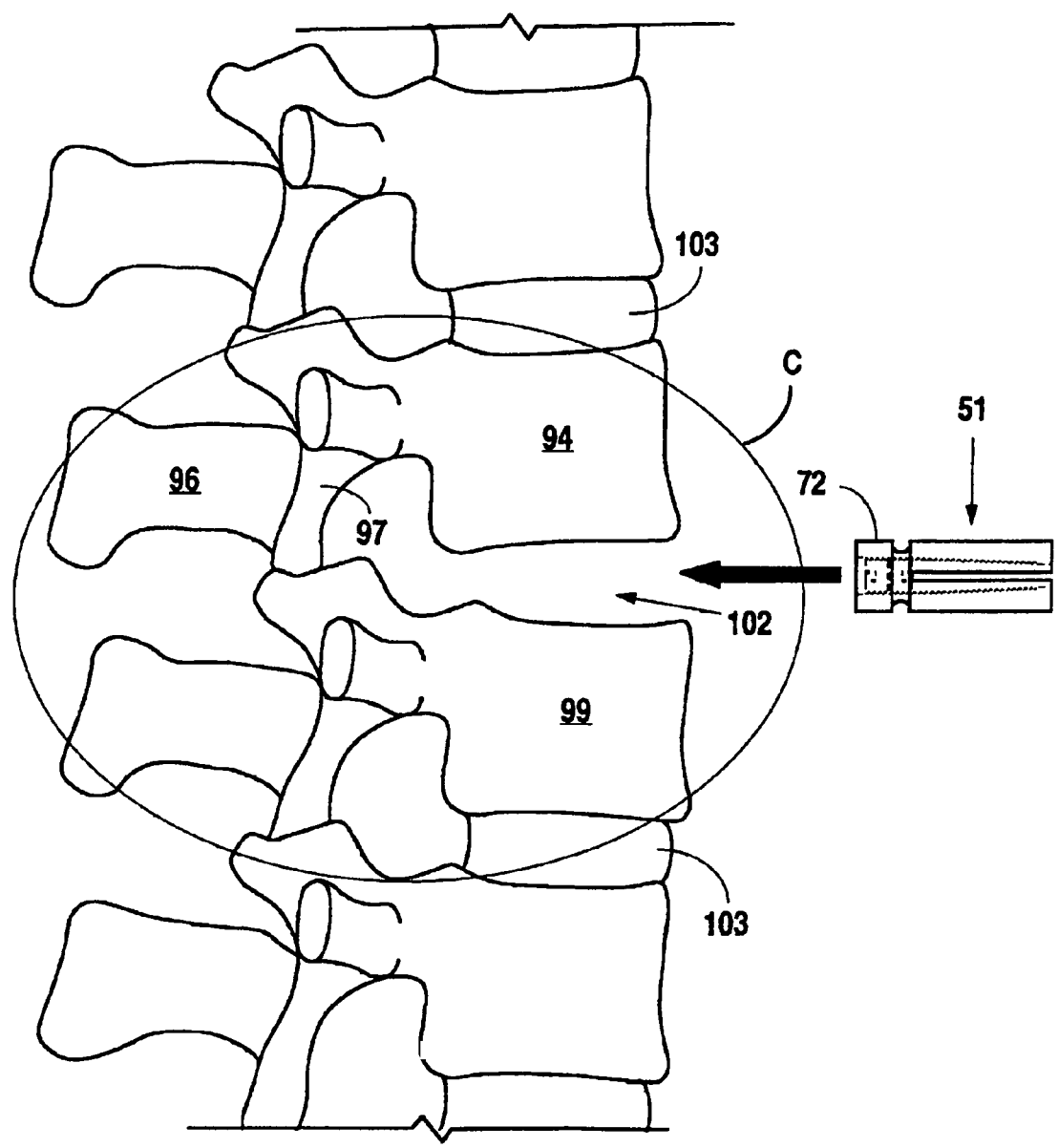
FIG. 21 shows, the path of an anterior insertion of the expandable lordosis stabilizing cage of FIG. 1 into the decompressed intervertebral disc space of a patient.
Figure 22:
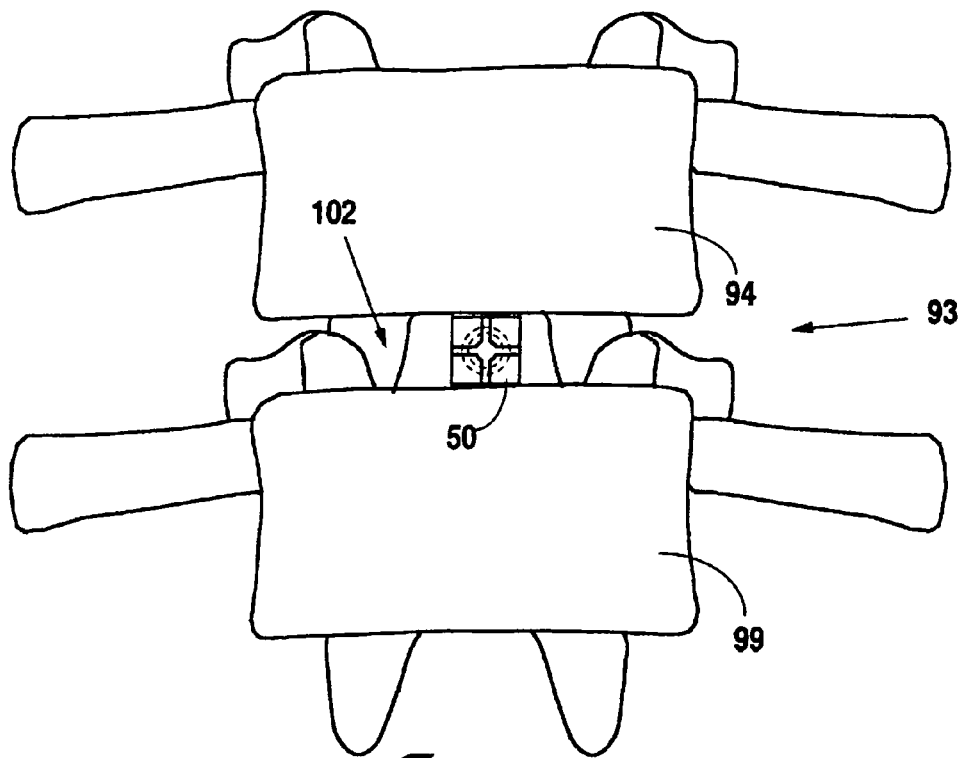
FIG. 22 shows, in an anterior elevational view of a section of assembled vertebrae, anterior placement of a single expandable lordosis stabilizing cage of FIG. 1 into the decompressed intervertebral disc space of a patient.
Figure 23:
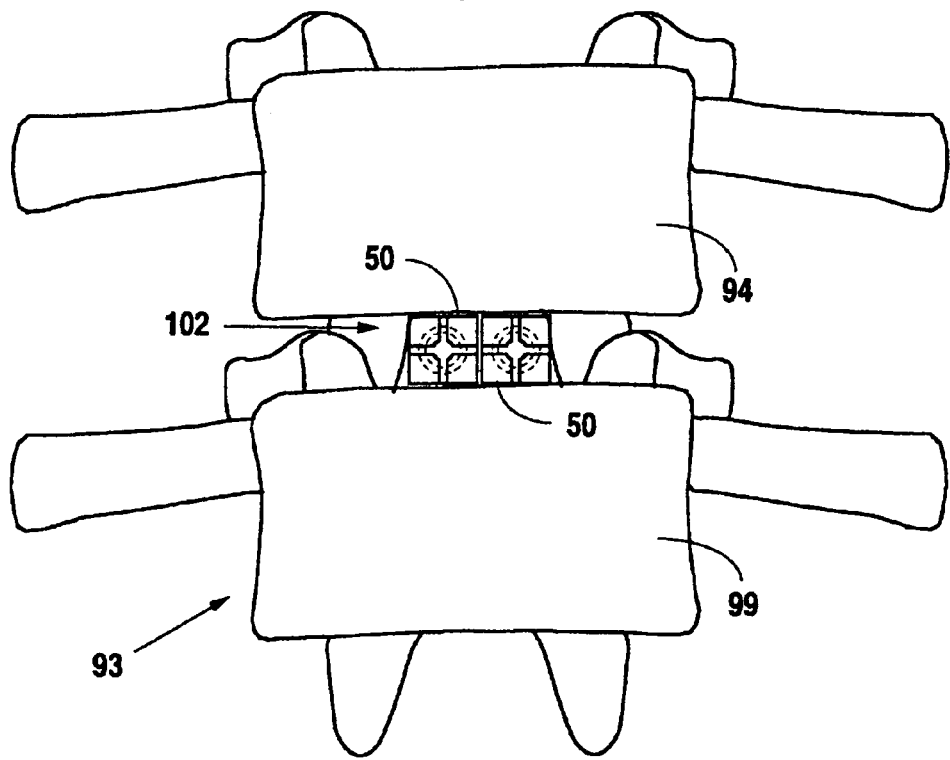
FIG. 23 shows, in an anterior elevational view of a section of assembled vertebrae, anterior placement of a pair of expandable lordosis stabilizing cages of FIG. 1 into the decompressed intervertebral disc space of a patient.

Referring now to FIGS. 19 through 27, the procedure for anterior insertion of the lordosis stabilizing cage 50 of the present invention into decompressed intervertebral disc space 102 between a superior vertebra 94 and an inferior vertebra 99 of a section of assembled vertebrae 93 is described. As shown in FIG. 19, the body of the lordosis stabilizing cage 50 is first prepared for anterior insertion by inserting the expansion wafer 81 (with the socket 85 of the expansion wafer 81 facing inward) into the orifice 74 of the nut 72 forming the fixed cage section 71. The expansion wafer 81 is threaded into the orifice 74 in position adjacent to the proximal end of the orifice 69 of the expandable cage section 52. As shown in FIG. 20, the end plug 86 is then inserted in place in the front face 73 of the fixed cage section 71.

With the body 51 of the lordosis stabilizing cage 50 prepared for insertion, the patient is prepared by surgically excising the affected intervertebral disc 103. It will be appreciated by those of ordinary skill in the art, anterior insertion of the lordosis stabilizing cage 50 of the present invention does not require surgical excision of the posterior bone structures as previously described with respect to posterior insertion. It is noted, however, that unlike a posterior insertion an anterior insertion carries the associated risk of surgery about delicate structures such as, for example, the patient's vena cava.

As shown in FIGS. 21 through 24, the prepared body 51 or a pair of prepared bodies 51 is then inserted (fixed cage section 71 first) into the decompressed intervertebral disc space 102. As particularly shown in FIGS. 22 and 23, the anterior insertion of the lordosis stabilizing cage 50 may be performed with a single generally square cross section stabilizing cage 91, a pair of the generally square cross section stabilizing cages 91 in side-by-side position or by insertion of a single generally rectangular cross section stabilizing cage 92, as has been described in detail with respect to FIGS. 28 through 34.

Figure 24:
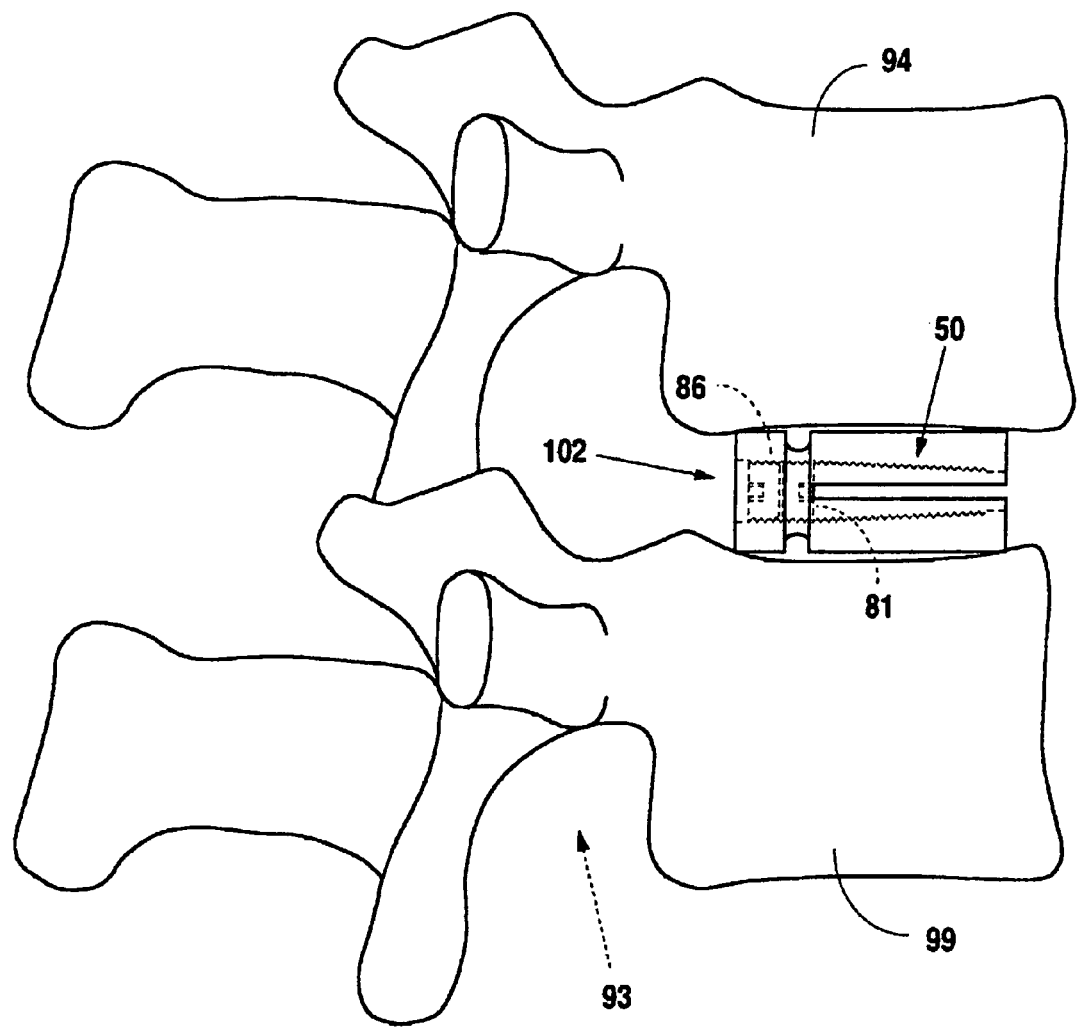
FIG. 24 shows, in a right side elevational detail view taken in detail area C of FIG. 21, placement into the decompressed intervertebral disc space of a patient of the body of the expandable lordosis stabilizing cage of FIG. 1 as prepared for posterior insertion according to FIG. 20.
Figure 25:
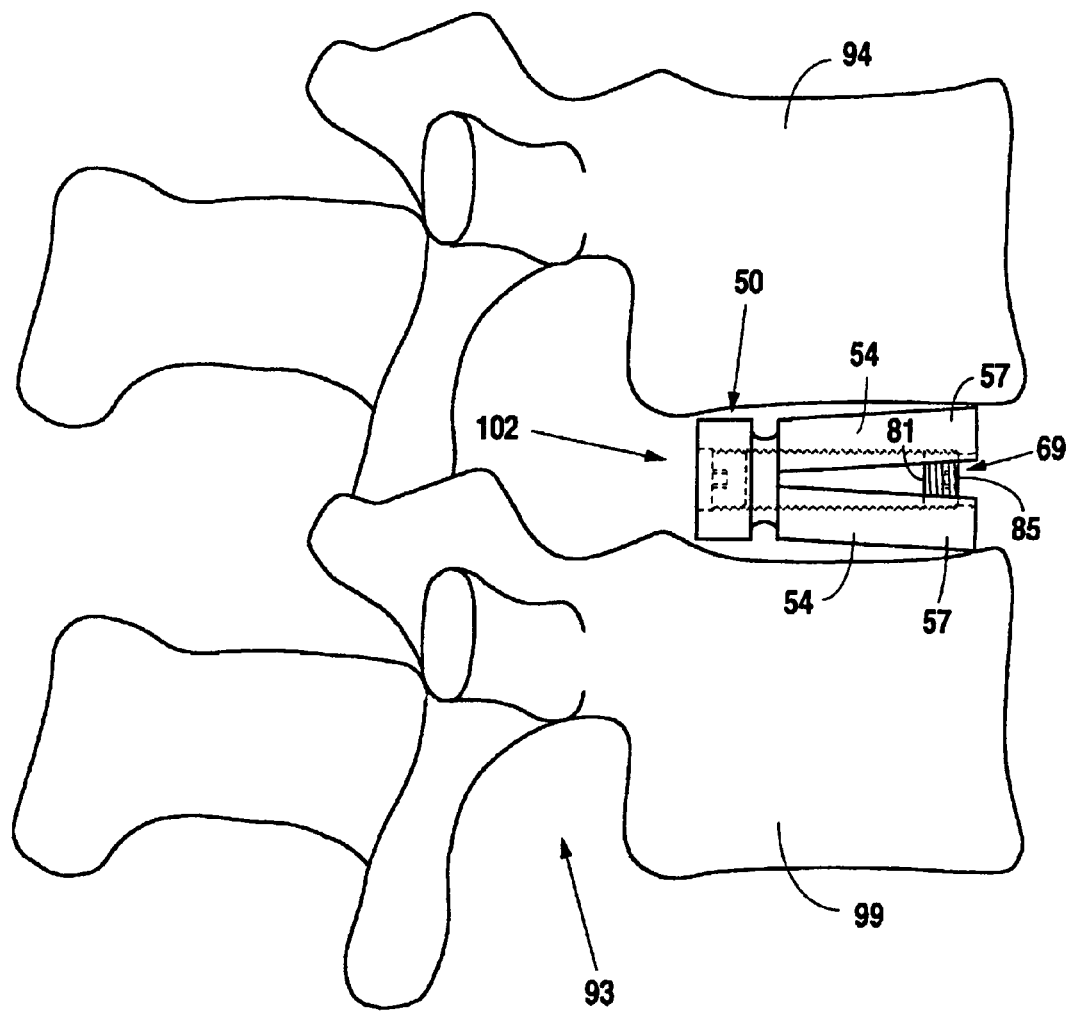
FIG. 25 shows, in a right side elevational detail view taken in detail area C of FIG. 21, expansion through operation of the expansion wafer of FIGS. 7 and 8 of the expandable cage section of the body of the expandable lordosis stabilizing cage of FIG. 1 after anterior insertion, the depicted placement being the final anterior insertion of the expandable lordosis stabilizing cage.
Figure 26:
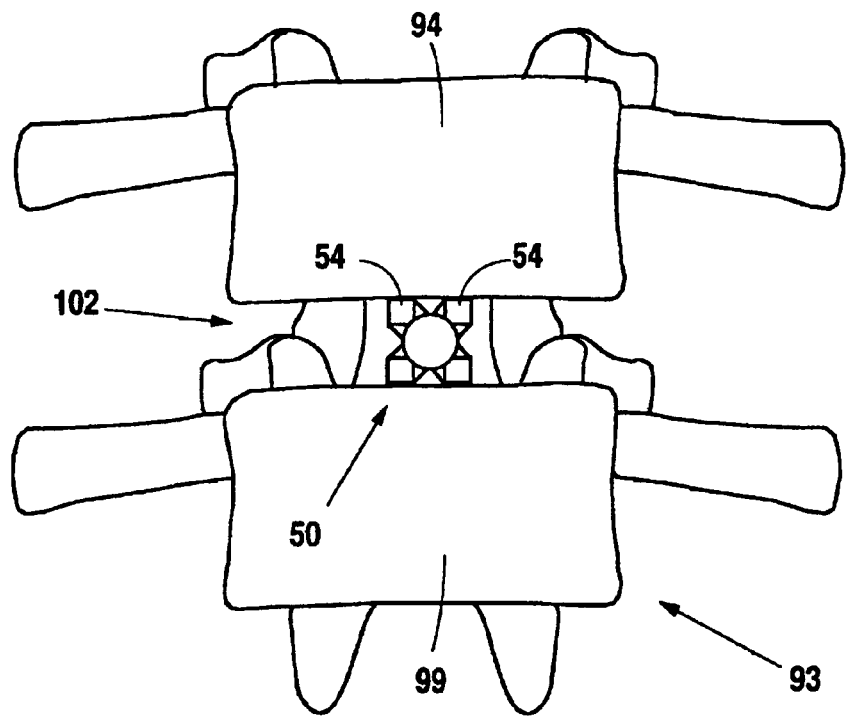
FIG. 26 shows, in an anterior elevational view of a section of assembled vertebrae, final anterior insertion of a single expandable lordosis stabilizing cage of FIG. 1.
Figure 27:
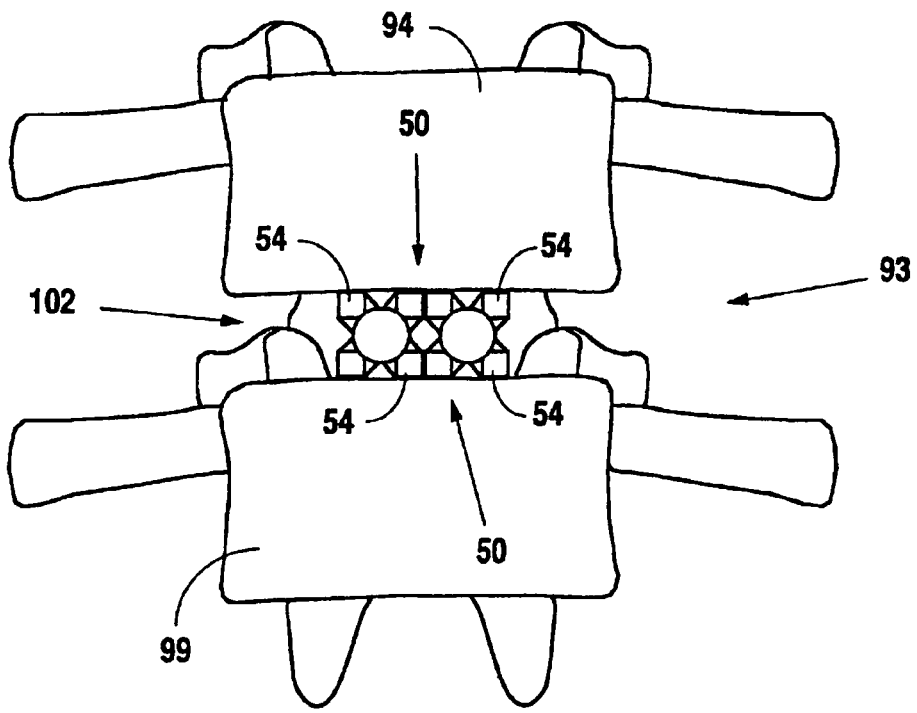
FIG. 27 shows, in an anterior elevational view of a section of assembled vertebrae, final anterior insertion of a pair of expandable lordosis stabilizing cages of FIG. 1.
Figure 28:
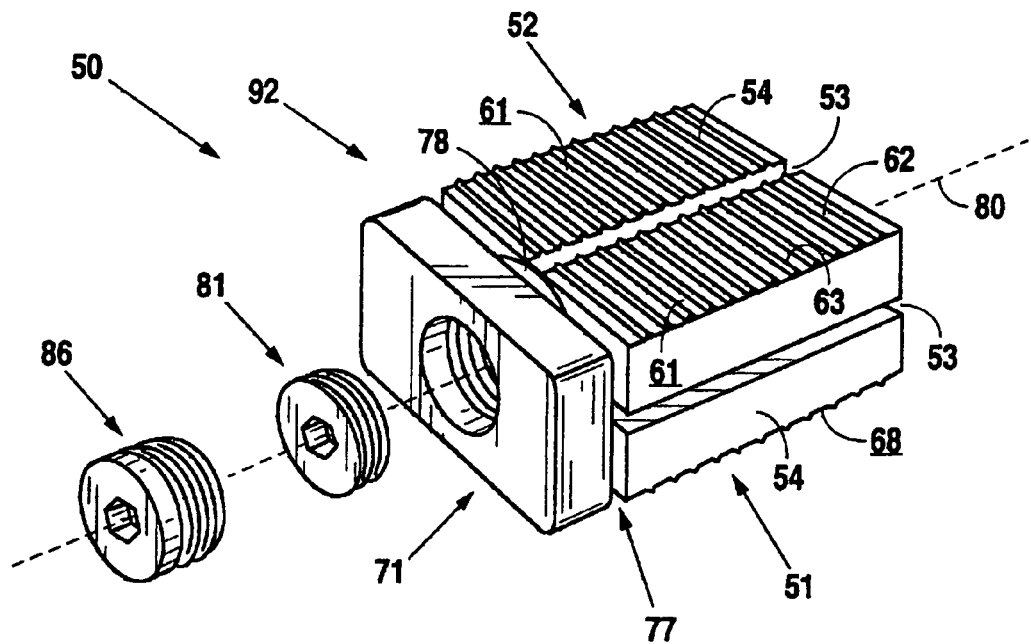
FIG. 28 shows, in a partially exploded perspective view, a second preferred embodiment of the expandable lordosis stabilizing cage of the present invention.
Figure 29:
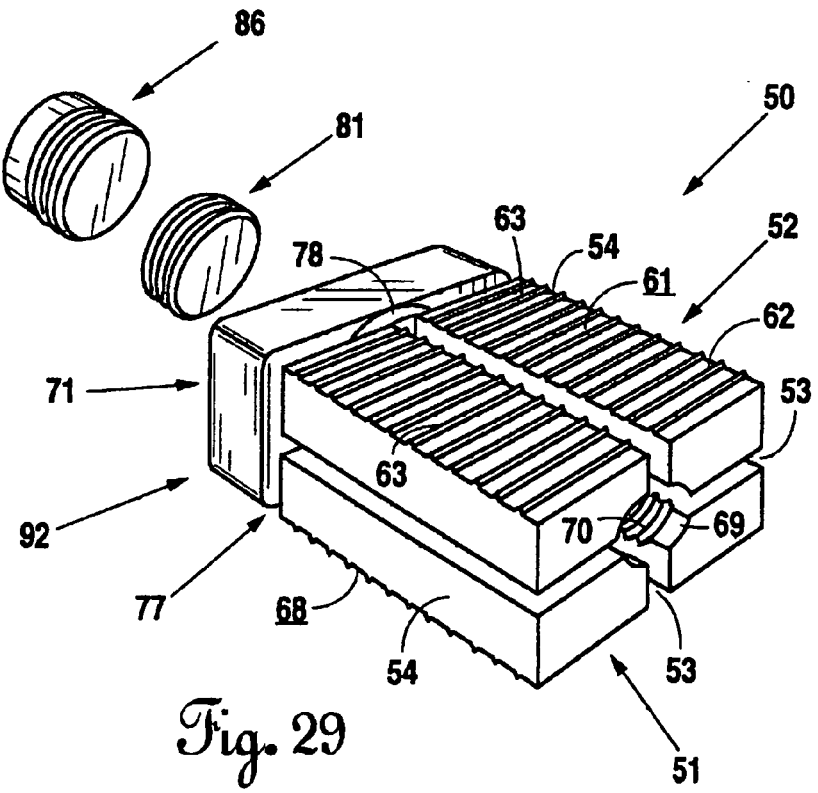
FIG. 29 shows, in a second partially exploded perspective view, the expandable lordosis stabilizing cage of FIG. 28.
Figure 35:
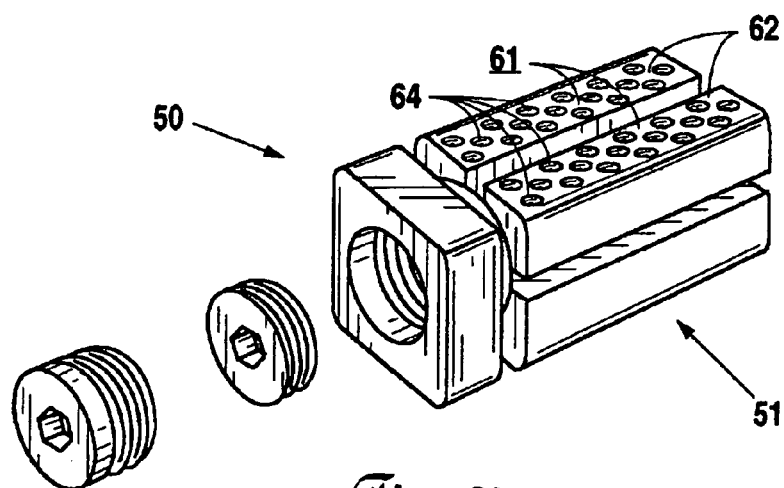
FIG. 35 shows, in a perspective view, the expandable lordosis stabilizing cage of FIG. 1 showing an alternative embodiment for implementation of irregularities on the upper surfaces of the upper pair of elongate blocks and the lower surfaces of the lower pair of elongate blocks of the expandable lordosis stabilizing cages of FIG. 1 or FIG. 28.
Figure 36:
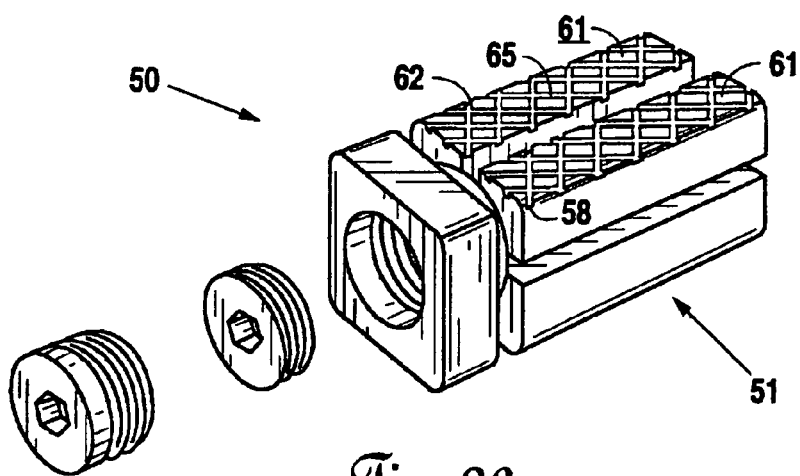
FIG. 36 shows, in a perspective view, the expandable lordosis stabilizing cage of FIG. 1 showing a second alternative embodiment for implementation of irregularities on the upper surfaces of the upper pair of elongate blocks and the lower surfaces of the lower pair of elongate blocks of the expandable lordosis stabilizing cages of FIG. 1 or FIG. 28.
Figure 37:
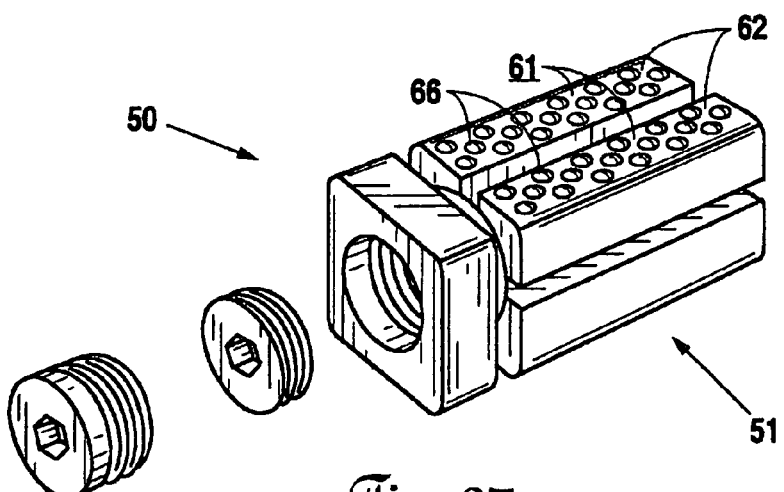
FIG. 37 shows, in a perspective view, the expandable lordosis stabilizing cage of FIG. 1 showing a third alternative embodiment for implementation of irregularities on the upper surfaces of the upper pair of elongate blocks and the lower surfaces of the lower pair of elongate blocks of the expandable lordosis stabilizing cages of FIG. 1 or FIG. 28.

In any case, with the previously prepared bodies 51 inserted into the intervertebral disc space 102 as depicted in FIG. 24, the surgeon then operates the expansion wafer 81 to translate the expansion wafer 81 through the orifice 69 of the expandable cage section 52 into position at the distal ends 57 of the elongate blocks 54, thereby radially outward flaring of the distal ends 57. Because in the anterior insertion of the lordosis stabilizing cage 50 it is necessary to draw the expansion wafer 81 toward the surgeon, the provision of threading in the orifices and about the expansion wafer 81 as previously described is particularly desirable for this procedure. In any case, the outward flaring of the distal ends 57 of the elongate blocks 54 in turn results in the wedging of the substantially planar surfaces 61 of the upper pair 60 of elongate blocks 54 and the substantially planar lower surfaces 68 of the lower pair 67 of elongate blocks 54 firmly between the superior vertebra 94 and the inferior vertebra 99 bounding the intervertebral disc space 102, as depicted in FIG. 25. As shown in FIGS. 25 through 27, upon final placement of the lordosis stabilizing cage or cages 50 of the present invention, the superior vertebra 94 and the inferior vertebra 99 will obtain and securely and stably maintain normal lordosis.

While the foregoing description is exemplary of the preferred embodiment of the present invention, those of ordinary skill in the relevant arts will recognize the many variations, alterations, modifications, substitutions and the like as are readily possible, especially in light of this description, the accompanying drawings and claims drawn thereto. For example, although poly-ether-ether-ketone is the presently preferred choice of material for construction of the expandable lordosis stabilizing cage of the present invention, those of ordinary skill in the art will recognize that other materials such as carbon fiber or titanium or any substantially equivalent material may also be utilized. In any case, because the scope of the present invention is much broader than any particular embodiment, the foregoing detailed description should not be construed as a limitation of the scope of the present invention, which is limited only by the claims appended hereto.

What is claimed is:

1. An expandable stabilizing cage for insertion into the intervertebral disc space of a patient for establishing and maintaining a desired lordosis, said expandable stabilizing cage comprising:
   a body having a fixed cage section, an expandable cage section and a relief between said fixed cage section and said expandable cage section, said expandable cage section comprising an upper pair of elongate blocks projecting from said fixed cage section and a lower pair of elongate blocks projection from said fixed cage section, each said pair having a left elongate block and a right elongate block, wherein:
      each one of said upper pair of elongate blocks comprises a substantially planar top surface;
      each one of said lower pair of elongate blocks comprises a substantially planar bottom surface;
      said upper pair of elongate blocks is separated from said lower pair of elongate blocks by a first longitudinal slot through said expandable cage section, said first longitudinal slot being positioned in a horizontal plane parallel with said central axis; and said left elongate blocks are separated from said right elongate blocks by a second longitudinal slot through said expandable cage section, said second longitudinal slot being positioned in a vertical plane parallel with said central axis;

an orifice through said body, said orifice being coaxial with a central longitudinal axis through said fixed cage section and said expandable cage section of said body;

an expansion wafer; and wherein:

said relief comprises an annulus formed coaxially about said orifice through said body, said annulus having an outside diameter that is less than the height top to bottom of said expandable cage section and is less than the width side to side of said expandable cage section, wherein:

each said elongate block comprises and end face; and each said elongate block interconnects with said fixed cage section at said annulus through a fractional portion of said end face of each respective elongate block;

each one of said upper pair of elongate blocks is positioned generally above one of said lower pair of elongate blocks;

a portion of said orifice through said expandable cage section is shaped in the form of a frustum of a cone, said portion of said orifice decreasing in diameter with increasing distance from said fixed cage section; and insertion of said expansion wafer into said orifice and from said fixed cage section into and through said expandable cage section causes radially outward flaring of said elongate blocks, said radially outward flaring causing said substantially planar surfaces of said elongate blocks to move nearer the vertebral bodies bounding the intervertebral disc space of the patient.

2. The expandable stabilizing cage as recited in claim 1, wherein said upper surfaces of said upper pair of elongate blocks and said lower surfaces of said lower pair of elongate blocks are provided with surface irregularities for facilitating stable engagement of said elongate blocks with adjacent vertebral bodies.

3. The expandable stabilizing cage as recited in claim 2, wherein said surface irregularities comprise denticles.

4. The expandable stabilizing cage as recited in claim 3, wherein said denticles are arranged transverse to said central longitudinal axis.

5. The expandable stabilizing cage as recited in claim 2, wherein said surface irregularities comprise dimples.

6. The expandable stabilizing cage as recited in claim 2, wherein said surface irregularities comprise scores.

7. The expandable stabilizing cage as recited in claim 2, wherein said surface irregularities comprise grooves.

8. The expandable stabilizing cage as recited in claim 2, wherein said surface irregularities comprise protuberances.

9. The expandable stabilizing cage as recited in claim 1, wherein a portion of said orifice through said body is provided with threading.

10. The expandable stabilizing cage as recited in claim 9, wherein said expansion wafer comprises a disc, said disc being circumferentially threaded.

11. The expandable stabilizing cage as recited in claim 10, wherein said expansion wafer comprises a drive on a first face thereof.

12. The expandable stabilizing cage as recited in claim 11, wherein said drive comprises a socket centrally provided on said first face.

13. The expandable stabilizing cage as recited in claim 12, wherein said socket comprises a hexagonal socket.

14. The expandable stabilizing cage as recited in claim 13, wherein said drive comprises a slot.

15. The expandable stabilizing cage as recited in claim 1, said expandable stabilizing cage further comprising an end plug for insertion into said orifice adjacent said fixed cage section.

16. The expandable stabilizing cage as recited in claim 1, wherein said expandable cage section comprises a generally rectangular transverse cross section.

17. The expandable stabilizing cage as recited in claim 1, wherein said expandable cage section comprises a generally square transverse cross section.

* * * * *